United States Patent
Wear et al.

(10) Patent No.: US 10,485,502 B2
(45) Date of Patent: Nov. 26, 2019

(54) SYSTEM AND METHOD FOR ASSESSING MUSCLE FUNCTION OF A PATIENT

(71) Applicant: General Electric Company, Schenectady, NY (US)

(72) Inventors: James Wear, Madison, WI (US); Serge Muller, Buc (FR); Randall Payne, Madison, WI (US); Paul Markwardt, Madison, WI (US)

(73) Assignee: General Electric Company, Schenectady, NY (US)

( * ) Notice: Subject to any disclaimer, the term of this patent is extended or adjusted under 35 U.S.C. 154(b) by 380 days.

(21) Appl. No.: 15/385,127

(22) Filed: Dec. 20, 2016

(65) Prior Publication Data

US 2018/0168530 A1   Jun. 21, 2018

(51) Int. Cl.
| | |
|---|---|
| A61B 6/00 | (2006.01) |
| A61B 5/22 | (2006.01) |
| A61B 5/11 | (2006.01) |
| A61B 5/0488 | (2006.01) |
| A61B 8/08 | (2006.01) |
| A61B 5/053 | (2006.01) |

(Continued)

(52) U.S. Cl.
CPC .............. *A61B 6/50* (2013.01); *A61B 5/0488* (2013.01); *A61B 5/0537* (2013.01); *A61B 5/112* (2013.01); *A61B 5/225* (2013.01); *A61B 5/4519* (2013.01); *A61B 6/4417* (2013.01); *A61B 6/482* (2013.01); *A61B 6/5217* (2013.01); *A61B 8/00* (2013.01); *A61B 8/08* (2013.01); *A61B 8/4416* (2013.01); *A61B 8/5223* (2013.01)

(58) Field of Classification Search
None
See application file for complete search history.

(56) References Cited

U.S. PATENT DOCUMENTS

| | | | |
|---|---|---|---|
| 6,850,798 B2 * | 2/2005 | Morgan | A01K 29/00 119/174 |
| 7,130,680 B2 * | 10/2006 | Kodama | A61B 5/0537 600/547 |

(Continued)

FOREIGN PATENT DOCUMENTS

| | | | |
|---|---|---|---|
| WO | 2012019071 A1 | 2/2012 | |
| WO | WO-2016092439 A1 * | 6/2016 | ........... A61K 39/395 |

*Primary Examiner* — Brian T Gedeon
(74) *Attorney, Agent, or Firm* — Grogan, Tuccillo & Vanderleeden, LLP

(57) ABSTRACT

A system for assessing muscle function of a patient is provided. The system includes: a dual-energy X-ray absorptiometry device operative to scan the patient so as to generate a lean mass measurement; a bioelectrical impedance analysis device operative to scan the patient so as to generate an extracellular water volume measurement; and a controller that includes at least one processor and a memory device, the controller in electrical communication with the dual-energy X-ray absorptiometry device and the bioelectrical impedance device. The controller is adapted to: receive the lean mass measurement and the extracellular water volume measurement; store the lean mass measurement and the extracellular water volume measurement in the memory device; and generate a muscle assessment indicator of the patient based at least in part on the lean mass measurement and the extracellular water volume measurement stored in the memory device.

20 Claims, 2 Drawing Sheets

Figure 1:
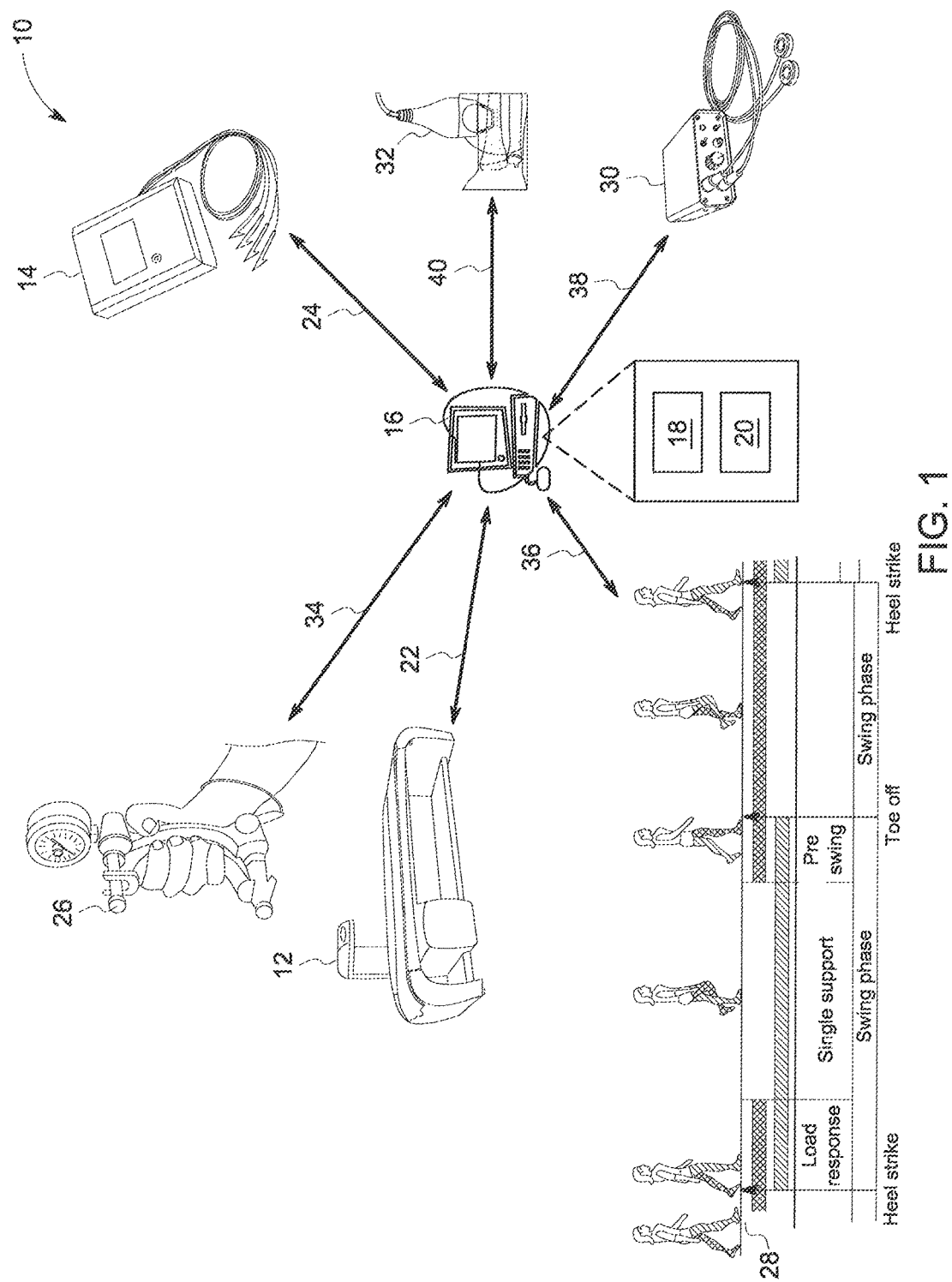

(51) Int. Cl.
*A61B 5/00* (2006.01)
*A61B 8/00* (2006.01)

(56) References Cited

U.S. PATENT DOCUMENTS

| | | | | |
|---|---|---|---|---|
| 7,657,292 B2* | 2/2010 | Baker, Jr. | ............. | A61B 5/0059 600/310 |
| 7,763,707 B2* | 7/2010 | Mintz | .................... | A61K 38/25 530/300 |
| 8,135,448 B2* | 3/2012 | Baker, Jr. | ............. | A61B 5/0059 600/310 |
| 8,175,665 B2* | 5/2012 | Baker, Jr. | ............. | A61B 5/0059 600/310 |
| 8,792,689 B2* | 7/2014 | Kelly | .................... | G06T 7/0012 382/128 |
| 8,835,485 B2 | 9/2014 | Springer et al. | | |
| 8,962,546 B2* | 2/2015 | Narkar | ................. | A61K 31/166 514/1.1 |
| 9,234,975 B2* | 1/2016 | De Meersman | ......... | G01V 1/36 |
| 9,579,347 B2* | 2/2017 | Pereira | ................. | A61K 38/018 |
| 9,591,987 B1* | 3/2017 | Liedtke | ................ | A61B 5/0537 |
| 9,826,806 B2* | 11/2017 | Challa | ...................... | A45B 9/04 |
| 9,974,463 B2* | 5/2018 | Rutkove | .............. | A61B 5/4519 |
| 10,053,506 B2* | 8/2018 | Smith | ................ | C07K 16/248 |
| 10,202,449 B2* | 2/2019 | Simard | ................ | C07K 16/245 |
| 2009/0018464 A1* | 1/2009 | Watanabe | ............ | A61B 5/0537 600/547 |
| 2011/0190655 A1* | 8/2011 | Moissl | ................. | A61B 5/0537 600/547 |
| 2012/0271192 A1* | 10/2012 | Just | ..................... | A61B 5/0536 600/547 |
| 2015/0045690 A1* | 2/2015 | Uchiyama | ............ | A61B 5/0537 600/547 |
| 2015/0150952 A1* | 6/2015 | Lewandowski | .... | A61K 38/1891 424/94.6 |
| 2016/0139154 A1* | 5/2016 | Hellerstein | ............ | G01N 33/70 506/12 |
| 2016/0349104 A1* | 12/2016 | Yuen | .................... | G06F 19/3418 |
| 2017/0273618 A1* | 9/2017 | Fullerton | ............... | A61B 6/482 |
| 2018/0049710 A1* | 2/2018 | Wilson | .................. | A61B 6/405 |
| 2018/0368729 A1* | 12/2018 | Wilson | .................. | A61B 6/482 |

* cited by examiner

SYSTEM AND METHOD FOR ASSESSING MUSCLE FUNCTION OF A PATIENT

BACKGROUND

Technical Field

Embodiments of the invention relate generally to muscular health, and more specifically, to a system and method for assessing muscle function of a patient.

Discussion of Art

Sarcopenia is a degenerative loss of skeletal muscle function, e.g., mass, quality, or strength, which is often considered a component of the frailty syndrome typically associated with aging and cachexia. Sarcopenia, however, may also occur in young and/or healthy individuals. Sarcopenia is typically diagnosed by assessing a patient's initial muscle function to obtain a baseline, and then comparing subsequent assessments of the patient's muscle function to the baseline. The patient is considered to have sarcopenia if their muscle function is found to be decreasing at a rate that exceeds an acceptable threshold, which is considered normal for the patient's age.

Sarcopenia, however, can be difficult to diagnose as there are a multitude of factors, such as muscle mass, quality, strength, etc., that determine the patient's level of muscle function. Moreover, while various methods and devices for assessing muscle function exists, no single method and/or device provides a generally accepted metric for describing muscle function. As a result, assessment of a patient's function is usually dependent on a clinician's ability to mentally interpret and combine various data sets produced by numerous differing devices, wherein differing sets of disparate devices may be used from one muscle function assessment procedure to the next.

What is needed, therefore, is an improved system and method for assessing muscle function of a patient.

BRIEF DESCRIPTION

In an embodiment, a system for assessing muscle function of a patient is provided. The system includes: a dual-energy X-ray absorptiometry device operative to scan the patient so as to generate a lean mass measurement; a bioelectrical impedance analysis device operative to scan the patient so as to generate an extracellular water volume measurement; and a controller that includes at least one processor and a memory device, the controller in electrical communication with the dual-energy X-ray absorptiometry device and the bioelectrical impedance device. The controller is adapted to: receive the lean mass measurement and the extracellular water volume measurement from the dual-energy X-ray absorptiometry device and the bioelectrical impedance analysis device, respectively; store the lean mass measurement and the extracellular water volume measurement in the memory device; and generate a muscle assessment indicator of the patient based at least in part on the lean mass measurement and the extracellular water volume measurement stored in the memory device.

In another embodiment, a method for assessing muscle function of a patient is provided. The method includes generating a lean mass measurement via scanning the patient with a dual-energy X-ray absorptiometry device; generating an extracellular water volume measurement via scanning the patient with a bioelectrical impedance analysis device; and receiving the lean mass measurement and the extracellular water volume measurement from the dual-energy X-ray absorptiometry device and the bioelectrical impedance analysis device, respectively, at a controller in electrical communication with the dual-energy X-ray absorptiometry device and the bioelectrical impedance analysis device, the controller including at least one processor and a memory device. The method further includes storing the lean mass measurement and the extracellular water volume measurement in the memory device; and generating a muscle assessment indicator of the patient based at least in part on the lean mass measurement and the extracellular water volume measurement stored in the memory device.

In yet another embodiment, a non-transitory computer readable medium is provided. The non-transitory computer readable medium stores instructions configured to adapt a controller, that includes at least one processor and a memory device, to: generate a lean mass measurement via scanning the patient with a dual-energy X-ray absorptiometry device in electrical communication with the controller; and generate an extracellular water volume measurement via scanning the patient with a bioelectrical impedance analysis device in electrical communication with the controller. The non-transitory computer readable medium further stores instructions configured to adapt the controller to receive the lean mass measurement and the extracellular water volume measurement from the dual-energy X-ray absorptiometry device and the bioelectrical impedance analysis device, respectively; store the lean mass measurement and the extracellular water volume measurement in the memory device; and generate a muscle assessment indicator of the patient based at least in part on the lean mass measurement and the extracellular water volume measurement stored in the memory device.

DRAWINGS

Figure 2:
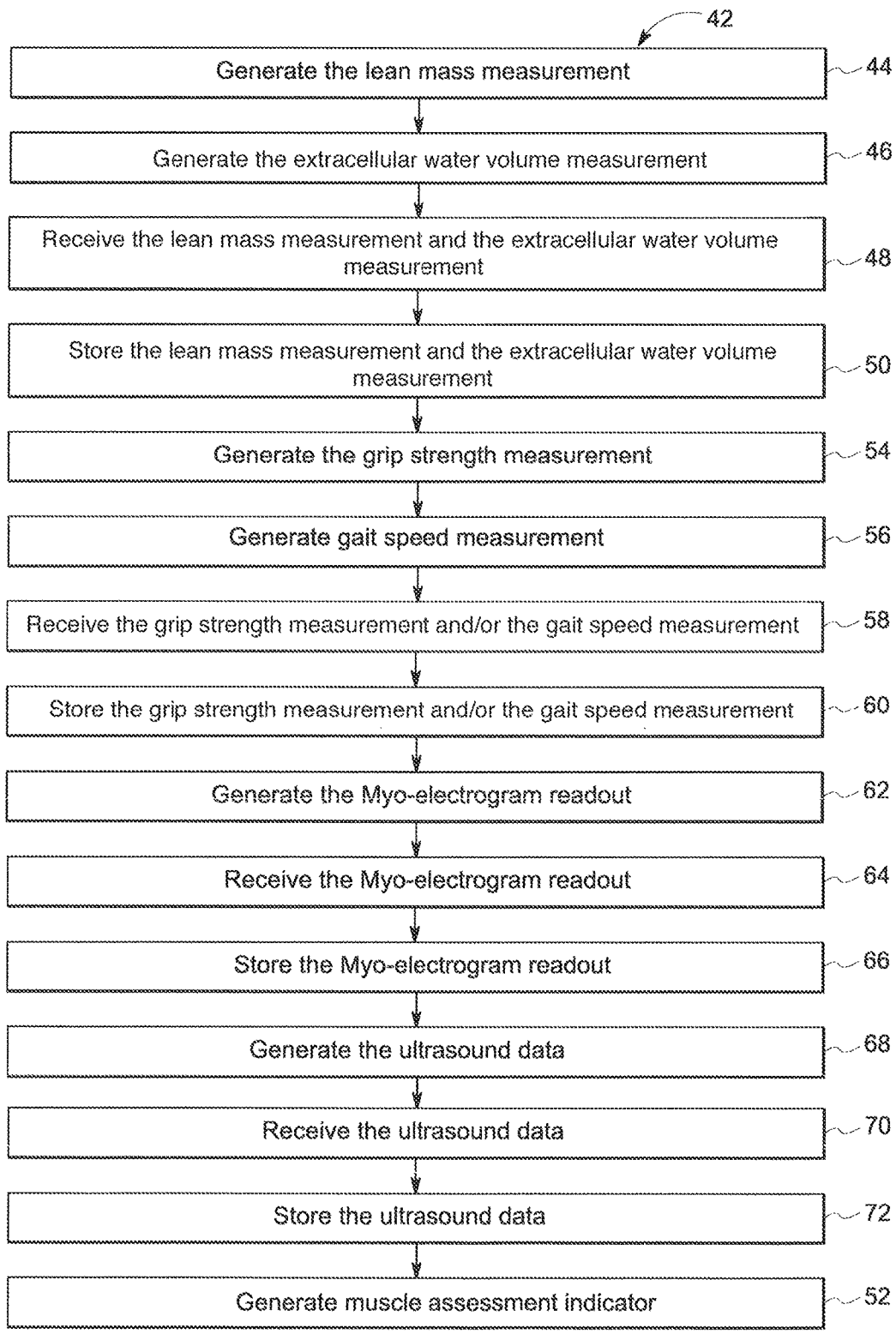

The present invention will be better understood from reading the following description of non-limiting embodiments, with reference to the attached drawings, wherein below:

FIG. 1 is a block diagram of an exemplary system for assessing muscle function of a patient in accordance with an embodiment of the invention; and FIG. 2 is a flow chart depicting a method for assessing muscle function of a patient utilizing the system of FIG. 1 in accordance with an embodiment of the invention.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, as will be appreciated, embodiments of the present invention may be used to analyze tissue, e.g., muscle, generally and are not limited to human tissue.

Referring now to FIG. 1, the major components of a system 10 for assessing muscle function of a patient according to an embodiment of the invention are shown. As shown in FIG. 1, the system 10 includes a duel-energy X-ray absorptiometry ("DXA") device 12, a bioelectrical impedance analysis ("BIS") device 14, and a controller 16. The controller 16 includes at least one processor 18 and a memory device 20, and electrically communicates with the DXA 12 and the BIS 14 via connections 22 and 24, respectively. In embodiments, the system 10 may further include a grip strength measuring device 26, a gait speed measuring device 28, a myo-electrogram device 30, and/or an ultrasound device 32 that electrically communicate with the controller 16 via connections 34, 36, 38, and 40, respectively. As will be appreciated, the connections 22, 24, 34, 36, 38, and/or 40 may be wired or wireless connections.

The DXA device 12 is operative to scan the patient so as to generate at least one of a lean mass measurement, a fat fraction measurement, a fat mass measurement, a fat free mass measurement, a bone mineral density measurement, a bone mineral content measurement, a body regional area measurement, a body thickness measurement, and a body volume measurement. In embodiments, the DXA device 12 may be of a standard form wherein the patient lies down on a bed/support platform while a scanner passes overhead and scans the patient utilizing x-rays of two different frequencies/energy levels.

The BIS device 14 is operative to scan the patient so as to generate at least one of an extracellular water volume measurement, an intracellular water volume measurement, and a total body water volume measurement. As will be appreciated, in embodiments, the BIS device 14 may include a plurality of electrodes connected to a controller. The electrodes are then connected to the patient so as to measure the electrical impedance, i.e., the opposition to the flow of an electric current through the patient's body tissues, which in turn can then be used to estimate the total body water ("TBW") of the patient. The TBW can then be used to estimate the amount of fat-free body mass, and by difference with the patient's body weight, the patient's body fat. As will be understood, the impedance of cellular tissue can be modeled as a resistor (representing the extracellular path) in parallel with a resistor and capacitor in series (representing the intracellular path).

The grip strength measuring device 26 is operative to measure at least one of a crush grip force of the patient, a pinch grip force of the patient, and a support grip force of the patient so as to generate a grip strength measurement. The crush grip force is generated by a handshake-type grip where the object being gripped rests firmly against the palm and all fingers. Generation of a pinch grip force involves placing the fingers of one of the patient's hands on a first side of an object, placing the thumb of the same hand on a different side of the object, and measuring the patient's ability to apply force to, i.e., "pinch," the object with the fingers and thumb. Generation of a support grip force involves the patient holding an object with their hand, such as the handle of a bucket, for a duration of time. As will be appreciated, measuring/assessing the support grip force provides an indication of the patient's muscular endurance.

The gait speed measuring device 28 is operative to measure a gait speed of the patient. As used herein, the term "gait speed" refers to a measurement of the speed at which the patient performs a pattern of movement, e.g., walking. As will be appreciated, the gait speed measuring device 28 may include a treadmill, a plurality of electrodes, and/or one or more cameras. In other embodiments, the gait speed measuring device 28 may record/measure the amount of time it takes the patient to perform a specified task/pattern of movement, e.g., walking ten meters. In such embodiments, the gait speed measuring device 28 may be a stopwatch and a computer, where the computer receives an electronic input corresponding to a time measured by the stopwatch for performing the specified task/pattern of movement.

The myo-electrogram device 30 is operative to measure electrical potential of the patient's muscles so as to generate a myo-electrogram readout. As will be appreciated, in embodiments, the myo-electrogram device 30 may include a plurality of electrodes configured to be attached to the patient. The myo-electrogram readout may indicate changes in the electrical potential of one or more of the patient's muscles over time.

The ultrasound device 32 is operative to scan the patient so as to generate ultrasound data. As will be appreciated, the ultrasound data may be used to generate one or more ultrasound images which in turn may be used to estimate the size and/or shape of specific muscles within the patient's body.

Turning now to FIG. 2, a method 42 of assessing muscle function of a patient utilizing the system 10 in accordance with an embodiment of the invention is shown. As shown in FIG. 2, the method includes generating 44 the lean mass measurement via scanning the patient with the DXA device 12; generating 46 the extracellular water volume measurement via scanning the patient with the BIS device 14; receiving 48 the lean mass measurement and the extracellular water volume measurement from the DXA device 12 and the BIS device 14, respectively, at the controller 16; storing 50, via the controller 16, the lean mass measurement and the extracellular water volume measurement in the memory device 20; and generating 52, via the controller 16, the muscle assessment indicator of the patient based at least in part on the lean mass measurement and the extracellular water volume measurement stored in the memory device 20.

As will be appreciated, in embodiments, generating 44 the lean mass measurement via the DXA device 12 may occur prior to generating 46 the extracellular water volume measurement via the BIS device 14. As will be understood, embodiments of the DXA device 12 may require the patient to lie down for an extended period of time, e.g., five (5) minutes or more, which may improve the quality of the extracellular water volume measurement taken by the BIS device 14.

As further shown in FIG. 2, in embodiments, the method 42 may further include generating 54 the grip strength measurement via measuring at least one of a crush grip force of the patient, a pinch grip force of the patient, and a support grip force of the patient via the grip strength measuring device 26; generating 56 the gait speed measurement via measuring the gait speed of the patient via the gait speed measuring device 28; receiving 58 the grip strength measurement and/or the gait speed measurement from the grip strength measuring device 26 and/or the gait speed measuring device 28, respectively, at the controller 16; and/or storing 60, via the controller 16, the grip strength measurement and/or the gait speed measurement in the memory device 20. As will be understood, in such embodiments, generating 52 the muscle assessment indicator via the controller 16 may be further based at least in part on the grip strength measurement and/or the gait speed measurement stored in the memory 20 device.

In embodiments, the method 42 may further include generating 62 the myo-electrogram readout via measuring electrical potential of the patient's muscles via the myo-electrogram device 30; receiving 64 the myo-electrogram readout from the myo-electrogram device at the controller 16; and storing 66, via the controller 16, the myo-electrogram readout in the memory device 20. As will be understood, in such embodiments, generating 52 the muscle assessment indicator via the controller 16 may be further based at least in part on the myo-electrogram readout stored in the memory 20 device.

In embodiments, the method 42 may further include generating 68 the ultrasound data via scanning the patient via the ultrasound device 32; receiving 70 the ultrasound data from the ultrasound device 32 device at the controller 16; and storing 72, via the controller 16, the ultrasound data in the memory device 20. As will be understood, in such embodiments, generating 52 the muscle assessment indicator via the controller 16 may be further based at least in part on the ultrasound data stored in the memory 20 device.

As will be appreciated, the muscle assessment indicator generated by the controller 16 may quantify the muscle performance of the patient. For example, in embodiments, the muscle assessment indicator may be an estimate of the likelihood that the patient has, and/or of the patient's risk of developing, a muscle pathology, e.g., sarcopenia, frailty, and/or cachexia. Further, in embodiments, the muscle assessment indicator may be in the form of an integrated report. Further, in embodiments, the muscle assessment indicator may be based upon weighted scores/measurements of one or more of the lean mass measurement, the extracellular water volume measurement, the grip strength measurement, the gait speed measurement, the myo-electrogram readout, and/or the ultrasound data. In such embodiments, the weight may determine how much a particular measurement impacts the muscle assessment indicator. Further, the weights of a first score/measurements may be based at least in part on a second score/measurement. For example, in embodiments, a higher weight may be given to the grip strength measurement if the lean mass measurement indicates that the patient has a high amount of lean muscle mass. Accordingly, a patient who has a high amount of lean muscle mass, but a low grip strength, is more likely to have a muscle pathology than another patient who has a low amount of lean muscle mass and a high grip strength.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system 10 may include at least one processor 18 (FIG. 1) and system memory/data storage structures 20 (FIG. 1), which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that provides for adapting the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for assessing muscle function of a patient is provided. The system includes: a dual-energy X-ray absorptiometry device operative to scan the patient so as to generate a lean mass measurement; a bioelectrical impedance analysis device operative to scan the patient so as to generate an extracellular water volume measurement; and a controller that includes at least one processor and a memory device, the controller in electrical communication with the dual-energy X-ray absorptiometry device and the bioelectrical impedance device. The controller is adapted to: receive the lean mass measurement and the extracellular water volume measurement from the dual-energy X-ray absorptiometry device and the bioelectrical impedance analysis device, respectively; store the lean mass measurement and the extracellular water volume measurement in the memory device; and generate a muscle assessment indicator of the patient based at least in part on the lean mass measurement and the extracellular water volume measurement stored in the memory device. In certain embodiments, the muscle assessment indicator quantifies muscle performance of the patient. In certain embodiments, the muscle assessment indicator is an estimate of at least one of the likelihood that the patient has a muscle pathology, and the risk that the patient will develop the muscle pathology. In certain embodiments, the muscle pathology is at least one of sarcopenia, frailty, and cachexia. In certain embodiments, the system further includes a grip strength measuring device in electrical communication with the controller and operative to measure at least one of a crush grip force of the patient, a pinch grip force of the patient, and a support grip force of the patient so as to generate a grip strength measurement. In such embodiments, the controller is further adapted to: receive the grip strength measurement from the grip strength measuring device; store the grip strength measurement in the memory device; and generate the muscle assessment indicator further based at least in part on the grip strength measurement stored in the memory device. In certain embodiments, the system further includes a gait speed measuring device in electrical communication with the controller and operative to measure a gait speed of the patient so as to generate a gait speed measurement. In such embodiments, the controller is further adapted to: receive the gait speed measurement from the gait speed measuring device; store the gait speed measurement in the memory device; and generate the muscle assessment indicator further based at least in part on the gait speed measurement stored in the memory device. In certain embodiments, the system further includes a myo-electrogram device in electrical communication with the controller and operative to measure electrical potential of the muscles of the patient so at to generate a myo-electrogram readout. In such embodiments, the controller is further adapted to: receive the myo-electrogram readout from the myo-electrogram device; store the myo-electrogram device in the memory device; and generate the muscle assessment indicator further based at least in part on the myo-electrogram readout stored in the memory device. In certain embodiments, the system further includes an ultrasound device in electrical communication with the controller and operative to scan the patient so as to generate ultrasound data. In such embodiments, the controller is further adapted to: receive the ultrasound data from the ultrasound device; store the ultrasound data in the memory device; and generate the muscle assessment indicator further based at least in part on the ultrasound data.

Other embodiments provide for a method for assessing muscle function of a patient. The method includes generating a lean mass measurement via scanning the patient with a dual-energy X-ray absorptiometry device; generating an extracellular water volume measurement via scanning the patient with a bioelectrical impedance analysis device; and receiving the lean mass measurement and the extracellular water volume measurement from the dual-energy X-ray absorptiometry device and the bioelectrical impedance analysis device, respectively, at a controller in electrical communication with the dual-energy X-ray absorptiometry device and the bioelectrical impedance analysis device, the controller including at least one processor and a memory device. The method further includes storing, via the controller, the lean mass measurement and the extracellular water volume measurement in the memory device; and generating, via the controller, a muscle assessment indicator of the patient based at least in part on the lean mass measurement and the extracellular water volume measurement stored in the memory device. In certain embodiments, generating a lean mass measurement via scanning the patient with a dual-energy X-ray absorptiometry device occurs prior to generating an extracellular water volume measurement via scanning the patient with a bioelectrical impedance analysis device, and the patient lies down while being scanned by the dual-energy X-ray absorptiometry device. In certain embodiments, the muscle assessment indicator quantifies muscle performance of the patient. In certain embodiments, the muscle assessment indicator is an estimate of at least one of the likelihood that the patient has a muscle pathology, and the risk that the patient will develop the muscle pathology. In certain embodiments, the muscle pathology is at least one of sarcopenia, frailty, and cachexia. In certain embodiments, the method further includes generating a grip strength measurement via measuring at least one of a crush grip force of the patient, a pinch grip force of the patient, and a support grip force of the patient via a grip strength measuring device in electrical communication with the controller; receiving the grip strength measurement from the grip strength measuring device at the controller; and storing, via the controller, the grip strength measurement in the memory device. In such embodiments, generating, via the controller, a muscle assessment indicator of the patient is further based at least in part on the grip strength measurement stored in the memory device. In certain embodiments, the method further includes generating a gait speed measurement via measuring a gait speed of the patient via a gait speed measuring device in electrical communication with the controller; receiving the gait speed measurement from the gait speed measuring device at the controller; and storing, via the controller, the gait speed measurement in the memory device. In such embodiments, generating, via the controller, a muscle assessment indicator of the patient is further based at least in part on the gait speed measurement stored in the memory device. In certain embodiments, the method further includes generating a myo-electrogram readout via measuring electrical potential of the muscles of the patient via a myo-electrogram device in electrical communication with the controller; receiving the myo-electrogram readout from the myo-electrogram device at the controller; and storing, via the controller, the a myo-electrogram readout in the memory device. In such embodiments, generating, via the controller, a muscle assessment indicator of the patient is further based at least in part on the myo-electrogram readout stored in the memory device. In certain embodiments, the method further includes: generating ultrasound data via scanning the patient via an ultrasound device in electrical communication with the controller; receiving the ultrasound data from the ultrasound device at the controller; and storing, via the controller, the ultrasound data in the memory device. In such embodiments, generating, via the controller, a muscle assessment indicator of the patient is further based at least in part on the ultrasound data stored in the memory device.

Yet still other embodiments provide for a non-transitory computer readable medium. The non-transitory computer readable medium stores instructions configured to adapt a controller that includes at least one processor and a memory device to: generate a lean mass measurement via scanning the patient with a dual-energy X-ray absorptiometry device in electrical communication with the controller; and generate an extracellular water volume measurement via scanning the patient with a bioelectrical impedance analysis device in electrical communication with the controller. The non-transitory computer readable medium further stores instructions configured to adapt the controller to receive the lean mass measurement and the extracellular water volume measurement from the dual-energy X-ray absorptiometry device and the bioelectrical impedance analysis device, respectively; store the lean mass measurement and the extracellular water volume measurement in the memory device; and generate a muscle assessment indicator of the patient based at least in part on the lean mass measurement and the extracellular water volume measurement stored in the memory device. In certain embodiments, the muscle assessment indicator is an estimate of at least one of the likelihood that the patient has a muscle pathology, and the risk that the patient will develop the muscle pathology. In certain embodiments, the muscle pathology is at least one of sarcopenia, frailty, and cachexia.

Accordingly, as will be appreciated, by providing a single system to measure various muscle function factors of a patient, some embodiments of the invention provide for a more efficient and streamlined method of determining whether a patient has a muscle pathology such as sarcopenia. Further, by utilizing a controller to combine/interpret the various measurements, e.g., the lean mass measurement, the extracellular water volume measurement, the grip strength measurement, the gait speed measurement, the myo-electrogram readout, and/or the ultrasound data to produce the muscle assessment indicator, some embodiments of the invention provide for a more standardized approach/method for diagnosing muscle pathologies. Additionally, some embodiments may provide for improved methods of assessing muscular rehabilitation therapies.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for assessing muscle function of a patient comprising:
    a dual-energy X-ray absorptiometry device operative to scan the patient so as to generate a lean mass measurement;
    a bioelectrical impedance analysis device operative to scan the patient so as to generate an extracellular water volume measurement;
    a controller that includes a processor and a memory device, the controller in electrical communication with the dual-energy X-ray absorptiometry device and the bioelectrical impedance device; and
    wherein the controller is adapted to:
        receive the lean mass measurement and the extracellular water volume measurement from the dual-energy X-ray absorptiometry device and the bioelectrical impedance analysis device, respectively;
        store the lean mass measurement and the extracellular water volume measurement in the memory device; and
        generate a muscle assessment indicator of the patient based at least in part on the lean mass measurement and the extracellular water volume measurement stored in the memory device.

2. The system of claim 1, wherein the muscle assessment indicator quantifies muscle performance of the patient.

3. The system of claim 1, wherein the muscle assessment indicator is an estimate of at least one of the likelihood that the patient has a muscle pathology, and the risk that the patient will develop the muscle pathology.

4. The system of claim 3, wherein the muscle pathology is at least one of sarcopenia, frailty, and cachexia.

5. The system of claim 1 further comprising:
    a grip strength measuring device in electrical communication with the controller and operative to measure at least one of a crush grip force of the patient, a pinch grip force of the patient, and a support grip force of the patient so as to generate a grip strength measurement;
    wherein the controller is further adapted to:
    receive the grip strength measurement from the grip strength measuring device;
    store the grip strength measurement in the memory device; and
    generate the muscle assessment indicator further based at least in part on the grip strength measurement stored in the memory device.

6. The system of claim 1 further comprising:
    a gait speed measuring device in electrical communication with the controller and operative to measure a gait speed of the patient so as to generate a gait speed measurement; and
    wherein the controller is further adapted to:
    receive the gait speed measurement from the gait speed measuring device;
    store the gait speed measurement in the memory device; and
    generate the muscle assessment indicator further based at least in part on the gait speed measurement stored in the memory device.

7. The system of claim 1 further comprising:
    a myo-electrogram device in electrical communication with the controller and operative to measure electrical potential of the muscles of the patient so at to generate a myo-electrogram readout; and wherein the controller is further adapted to:
receive the myo-electrogram readout from the myo-electrogram device;
store the myo-electrogram device in the memory device; and
generate the muscle assessment indicator further based at least in part on the myo-electrogram readout stored in the memory device.

8. The system of claim 1 further comprising:
an ultrasound device in electrical communication with the controller and operative to scan the patient so as to generate ultrasound data; and
wherein the controller is further adapted to:
receive the ultrasound data from the ultrasound device;
store the ultrasound data in the memory device; and
generate the muscle assessment indicator further based at least in part on the ultrasound data.

9. A method for assessing muscle function of a patient comprising:
generating a lean mass measurement via scanning the patient with a dual-energy X-ray absorptiometry device;
generating an extracellular water volume measurement via scanning the patient with a bioelectrical impedance analysis device;
receiving the lean mass measurement and the extracellular water volume measurement from the dual-energy X-ray absorptiometry device and the bioelectrical impedance analysis device, respectively, at a controller in electrical communication with the dual-energy X-ray absorptiometry device and the bioelectrical impedance analysis device, the controller including at least one processor and a memory device;
storing the lean mass measurement and the extracellular water volume measurement in the memory device; and
generating a muscle assessment indicator of the patient based at least in part on the lean mass measurement and the extracellular water volume measurement stored in the memory device.

10. The method of claim 9, wherein generating a lean mass measurement via scanning the patient with a dual-energy X-ray absorptiometry device occurs prior to generating an extracellular water volume measurement via scanning the patient with a bioelectrical impedance analysis device, and the patient lies down while being scanned by the dual-energy X-ray absorptiometry device.

11. The method of claim 9, wherein the muscle assessment indicator quantifies muscle performance of the patient.

12. The method of claim 9, wherein the muscle assessment indicator is an estimate of at least one of the likelihood that the patient has a muscle pathology, and the risk that the patient will develop the muscle pathology.

13. The method of claim 12, wherein the muscle pathology is at least one of sarcopenia, frailty, and cachexia.

14. The method of claim 9 further comprising:
generating a grip strength measurement via measuring at least one of a crush grip force of the patient, a pinch grip force of the patient, and a support grip force of the patient via a grip strength measuring device in electrical communication with the controller;
receiving the grip strength measurement from the grip strength measuring device at the controller;
storing, via the controller, the grip strength measurement in the memory device; and
wherein generating, via the controller, a muscle assessment indicator of the patient is further based at least in part on the grip strength measurement stored in the memory device.

15. The method of claim 9 further comprising:
generating a gait speed measurement via measuring a gait speed of the patient via a gait speed measuring device in electrical communication with the controller;
receiving the gait speed measurement from the gait speed measuring device at the controller;
storing, via the controller, the gait speed measurement in the memory device; and
wherein generating, via the controller, a muscle assessment indicator of the patient is further based at least in part on the gait speed measurement stored in the memory device.

16. The method of claim 9 further comprising:
generating a myo-electrogram readout via measuring electrical potential of the muscles of the patient via a myo-electrogram device in electrical communication with the controller;
receiving the myo-electrogram readout from the myo-electrogram device at the controller;
storing, via the controller, the a myo-electrogram readout in the memory device; and
wherein generating, via the controller, a muscle assessment indicator of the patient is further based at least in part on the myo-electrogram readout stored in the memory device.

17. The method of claim 9 further comprising:
generating ultrasound data via scanning the patient via an ultrasound device in electrical communication with the controller;
receiving the ultrasound data from the ultrasound device at the controller;
storing, via the controller, the ultrasound data in the memory device; and
wherein generating, via the controller, a muscle assessment indicator of the patient is further based at least in part on the ultrasound data stored in the memory device.

18. A non-transitory computer readable medium storing instructions configured to adapt a controller that includes at least one processor and a memory device to:
generate a lean mass measurement via scanning the patient with a dual-energy X-ray absorptiometry device in electrical communication with the controller;
generate an extracellular water volume measurement via scanning the patient with a bioelectrical impedance analysis device in electrical communication with the controller;
receive the lean mass measurement and the extracellular water volume measurement from the dual-energy X-ray absorptiometry device and the bioelectrical impedance analysis device, respectively;
store the lean mass measurement and the extracellular water volume measurement in the memory device; and
generate a muscle assessment indicator of the patient based at least in part on the lean mass measurement and the extracellular water volume measurement stored in the memory device.

19. The non-transitory computer readable medium of claim 18, wherein the muscle assessment indicator is an estimate of at least one of the likelihood that the patient has a muscle pathology, and the risk that the patient will develop the muscle pathology.

20. The non-transitory computer readable medium of claim 19, wherein the muscle pathology is at least one of sarcopenia, frailty, and cachexia.

\* \* \* \* \*